United States Patent [19]
LeBrun et al.

[11] Patent Number: 5,460,824
[45] Date of Patent: Oct. 24, 1995

[54] METHOD FOR THE PREPARATION OF AN ENCAPSULATED MEDICAMENT

[75] Inventors: Jean C. LeBrun, Greenwood; Jackie L. Massey, Hodges, both of S.C.

[73] Assignee: Warner-Lambert Company, Morris Plains, N.J.

[21] Appl. No.: 544,307

[22] Filed: Jun. 27, 1990

[51] Int. Cl.$^6$ ..................................................... A61K 9/48
[52] U.S. Cl. .......................... 424/453; 424/454; 424/456; 424/478; 514/962; 53/454; 53/440
[58] Field of Search ................................... 424/451, 454, 424/453, 456, 474, 478, 463, 475, 452; 514/962; 53/419, 441, 440, 454, 471

[56] References Cited

U.S. PATENT DOCUMENTS

| | | | |
|---|---|---|---|
| 3,071,513 | 1/1963 | De Boer et al. | 424/454 |
| 4,609,417 | 9/1986 | Smith | 156/69 |
| 4,756,902 | 7/1988 | Harvey et al. | 424/454 |
| 4,928,840 | 5/1990 | Barshay et al. | 220/8 |
| 4,936,074 | 6/1990 | Graham | 424/454 X |
| 4,965,089 | 10/1990 | Sauter et al. | 424/451 X |
| 4,966,771 | 10/1990 | Berta | 424/478 |

OTHER PUBLICATIONS

Handbook of Chemistry and Physics, Weast, Robert C., CRC Press, Jan. 1977 p. E–45.

*Primary Examiner*—Gollamudi S. Kishore
*Assistant Examiner*—James M. Spear
*Attorney, Agent, or Firm*—Charles W. Almer, III

[57] ABSTRACT

A tamper-resistant, caplet like medicament that masks the taste of poor tasting drugs and possesses an improved lubricity for easier swallowing is produced by shrinking a gelatin-based capsule about a caplet-shaped tablet of the medicament at specific temperatures, pressure and relative humidity.

9 Claims, No Drawings

1

METHOD FOR THE PREPARATION OF AN ENCAPSULATED MEDICAMENT

FIELD OF THE INVENTION

The present invention is related to coated or encapsulated pharmaceuticals that can be administered in a caplet-type dosage form. A novel method for preparing gelatin coated pharmaceuticals and the caplets prepared thereby offers tamper-resistance protection and greater ease in swallowing so as to encourage better patient compliance.

BACKGROUND OF INVENTION

The use of hard gelatin capsules for the containment of pharmaceuticals in unit dosage forms has been known for years. As opposed to tablets wherein the medicament is itself compressed into an ovoid or elliptical cylinder and swallowed directly, solid gelatin capsules have been used to administer pharmaceuticals in many different forms such as powders, liquids, oils and the like. As opposed to tablets, capsules completely envelop the drug until it reaches the stomach wherein the gelatin coating is eventually dissolved thereby releasing the medicament for absorption into the bloodstream. This provides an additional benefit of not only taste-masking many otherwise bitter tasting or unpalatable pharmaceuticals but also provides a lubricious mouth-feel or texture to the surface of the medicament for easier swallowing and passage into the digestive system.

Standard capsules known in the art are prepared by dipping rows of stainless steel pins into solutions of gelatin, starch gelatin or gelatin glycerin. The pins are removed from solution, the dipped portion dried and stripped off the pin. Both capsule halves are formed in this manner. One half is generally referred to as the capsule "body" while the half that fits over the open end of the first is referred to as the "cap". The cap is mated with the body by fitting over its open end. The capsules are generally sold in this assembled manner and the drug or medicament filled later. Commercially available capsule making machines are manufactured by Cherry-Burrell, Cedar Rapids, Iowa 52406 for example.

A drawback in the use of hard gelatin capsules become frighteningly evident several years ago when several people died taking a well known, over-the-counter analgesic that had been laced with cyanide through tampering. The problem that exists in standard capsule technology of the art is that the two halves of a gelatin capsule can be pulled apart and the medicament exposed. Anything can be added or detracted from the composition at this point and the halves then compressed together to again form one whole capsule. Moreover, there is nothing that would indicate the composition inside the gelatin capsule had been changed so as to serve as a warning to any unsuspecting patient or consumer, i.e. there is no tamper-evident indication incorporated into most commercially available gelatin capsules.

The cyanide tampering incidents forced many if not all prescription and over-the-counter pharmaceutical manufacturers to take additional packaging steps to insure that such tampering could not occur without it at least being noticed by the otherwise unsuspecting patient prior to a possibly fatal consumption. "Blister packs", safety sealed bottles and other forms of safety packaging rapidly appeared throughout the pharmaceutical industry in an effort to prevent any further tampering. Capsule products were withdrawn from the market altogether and in some cases were replaced by "caplets", solid oblong tablets comprised of the medicament and coated with a material such as cellulose, pectin, etc. The solid form of the drug not only protected against further tampering since the caplet would have to be broken apart in order to incorporate any additional ingredients and this lack of caplet integrity is easily discernible, but the coating also provides an ease in swallowing and protected some medicaments such as aspirin from causing stomach distress.

However, all of these reactionary measures and their precautions have added additional expense to the manufacture and packaging of both prescription and over-the-counter drugs. U.S. Pat. No. 4,820,524 to Berta points out that beyond the additional cost factors of these precautions, consumer surveys suggest that the shiny, familiar capsule shape has a special appeal to patients as being easy to swallow. It is additionally theorized that consumers perceive capsuled medicaments as being more effective in light of the long term association of the capsule with many well known and well respected pharmaceutical companies and their products. This could possibly add an additional placebo factor to their actual effectiveness. There exists then, a very real need for truly tamper-resistant capsule or capsule-like encapsulating materials as carriers for pharmaceuticals and other medicaments.

A number of references have coated pills or tablets by dipping them into gelatin solutions of one type or another. U.S. Pat. No. 599,865 to Richards discloses an apparatus for coating pills with gelatin whereby a bar is coated with an adhesive which holds the pills to be coated in place. The bar is then fitted over a second plate containing holes to which the affixed pills are aligned. The bar and plate, once joined, immerse half of the pill body into the gelatin. The bar and plate are then inverted whereby the other half is coated. Whereas the process may coat the pills with a material such as cellulose, starch, etc., there is no indication that a capsule-like appearance is achieved. Moreover, the process must be carried out manually and in no way could meet the production demands of today's world.

Of particular interest is U.S. Pat. No. 4,820,520 to Berta wherein a solid medicament core such as a caplet is provided with a capsule-like coating by dipping first one end of the capsule into a gelatinous solution so as to cover one-half of the caplet. This is then dried and the other end is dipped into the solution so that both gelatinous "dips" over-lap at approximately the midway point of the longitudinal axis of the caplet. This over-lapping of the gelatin coats is perceived as the seam created when two solid gelatin capsule halves are joined in the traditional procedure known in the art. U.S. Pat. No. 4,867,983 also to Berta discloses the method whereby the caplet is coated with a first gelatinous core on one end followed by the coating of a second gelatinous core on the other end which is thicker than the first so as to simulate the interlocking halves of a hollow gelatin capsule. The dipping procedure however, must be precise and requires intricate processing and mechanical steps in order to guarantee a smooth gel coating about the caplet. Since two dipping steps are required, the likelihood of uneven coating about the caplet remains high and many caplets are not assured of consistency in capsule shape and size.

It is an object of the present invention to provide a tamper-resistant pharmaceutical capsule whereby a medicament in the form of a caplet, is encapsulated with a solid gelatin capsule which is essentially tasteless and easy to swallow.

It is a further object of the present invention to provide a method for encapsulating a medicament in the form of a caplet with a solid gelatin capsule by shrinking said capsule about said caplet with no space therebetween.

It is yet a further object of the present invention to provide a capsule-like medicament wherein two solid gelatin capsule halves are fused about the caplet and cannot be removed without substantial damage thereto.

It is yet a further object of the present invention to provide a method for the preparation of a tamper-resistant capsule about a solid medicament in the form of a caplet by shrinking said capsule at a specific temperature and relative humidity so as to insure uniform shrinkage and fusion of said capsule about said caplet.

SUMMARY OF THE INVENTION

The present invention presents a novel method for the encapsulation of a solid pharmaceutical or over-the-counter drug in a solid gelatin capsule so as to provide a tamper-resistant coating that has the additional advantages of ease in swallowing, taste masking and aesthetic desirability. The method requires the application of energy in the form of heat for a critical time at a constant relative humidity so as to insure uniform shrinkage of the capsule around the drug. The inner surface of the capsule bonds to the surface of the caplet while the two portions of the capsule halves that over lap bond to each other forming a contiguous and continuous intact coating about the drug.

DETAILED DESCRIPTION OF THE INVENTION

The present invention deals with the shrinking of solid, hard gelatin, starch, starch gelatin or gelatin glycerin capsules about a solid pharmaceutical or over-the-counter drug so as to provide several advantages over the uncoated caplets known in the art. For one, the gelatin capsules are tasteless so that by shrinking these capsules about an otherwise bad tasting drug, the patient's taste buds are insulated from the bad taste of the drug as it passes through the oral cavity. The capsule does not dissolve or disintegrate until it reaches the stomach and is well past the organoleptic sensory system. Secondly, the fused capsules provide a tamper-resistant feature to any drug so coated since any attempt to incorporate a foreign substance into one of the capsules of the present invention can only damage the integrity of the capsule which is readily noticed. The encapsulated pharmaceuticals and drugs of the present invention are slowly dissolved in the stomach due to the presence of the gelatin capsule and this reduces the likelihood of stomach distress associated with many of the analgesics such as aspirin.

Moreover, the shiny aesthetic features of the capsule shaped medicament have been long associated with well known and trusted products of the pharmaceutical industry and it is believed that this association acts as additional psychological placebo factor in the drugs' actual effectiveness i.e., by encouraging better patient compliance. And finally, along these lines, the capsules inherently possess a certain ease in swallowing due to the lubricious nature of the gelatin coat and this can only serve to further encourage patient compliance.

The core material can be any prescription pharmaceutical, over-the-counter drug, flavoring agent or sweetener so long as it can be compressed into a solid, oblong cylindrical form known in the industry as a caplet. Suitable medicaments may be antihypertensives, analgesics, antibiotics, anti-tussives antiarrythmics, antihistamines, antacids, decongestants, laxatives, vitamins, mineral supplements, mixtures thereof and the like. Whereas prescription pharmaceuticals and over-the-counter drugs comprise the preferred embodiments of the present invention, solid forms of sweeteners or flavoring agents may be so encapsulated so as to improve their stability or delay their release rates in certain environments.

It has been determined that temperature, relative humidity and capsule moisture content are critical parameters in the shrinkage encapsulation process. Numerous capsule defects arise during the process of the present invention unless all of these parameters fall within specified ranges. Generally, these defects are attributable to one of the following.

In one instance, air can become trapped inside the solid gelatin capsule during shrinkage which forms pockets or corrugations on the capsule surface, leaving an unsightly blemish that disrupts the integrity of the capsule and is commercially unacceptable. A second problem encountered is that of the short overlap defect whereby one-half of the solid gelatin capsule may shrink more than the other cap or body half resulting in no sectional overlap or a non-fused capsule at or about the midpoint of the longitudinal axis of the caplet. This enables one to pull the capsule apart and is obviously unacceptable.

Another problem encountered is that the edges of the cap portion, which generally overlap a portion of the body thereby forming a collar about the mid-point of the longitudinal axis of the caplet, do not stick to the body but flange outward from the capsule after shrinkage. Generally, bonding of the capsule cap with the caplet has occurred but the flange is both unsightly and will interfere with proper swallowing of the medicament.

For purposes of this invention, the term "hard gelatin" capsule is meant to include any conventional hard capsule which is capable of being shrunk, using the present inventive process. For example, capsules comprised of gelatin, starch, sugar gelatin, gelatin glycerin and mixtures thereof are useful in the practice of the present invention.

Generally, the two capsule parts can be of identical or different colors, transparent or opaque. The hard gelatin capsules found to be of greatest value in the practice of the present invention are those registered under the trade name Supro C and are manufactured by the Capsugel Co. of Greenwood, S.C. Capsule size can be varied according to the dosage of the caplet to be coated. The moisture content of the hard gelatin capsules useful in the practice of the present invention can vary from about 13.0% to approximately 16.0% and preferably varies from about 14.0 to about 15.0%. Table 1 below is indicative of the amount of water in each of five (5) representative capsule sizes useful in the practice of the present invention together with the capsule weight of the final product as dictated by the density of the core material.

TABLE I

CONI-SNAP SUPRO ™
CAPSULE WEIGHT CAPACITY MG

| CAP-SULE SIZE | CAPSULE VOLUME | POWDER DOSE DENSITY | | | |
|---|---|---|---|---|---|
| | | 0.6 g/cc | 0.8 g/cc | 1.0 g/cc | 1.2 g/cc |
| A | 0.68 | 408 | 544 | 680 | 816 |
| B | 0.50 | 300 | 400 | 500 | 600 |
| C | 0.37 | 222 | 296 | 370 | 444 |
| D | 0.30 | 180 | 240 | 300 | 360 |
| E | 0.21 | 126 | 168 | 210 | 252 |

The two halves of the hard gelatin capsules once selected according to the size of the caplet to be coated can be placed about the two ends of the caplet core either manually or mechanically by making minor modifications to any one of a number of commercially available machines known in the art such as capsule filling machines from Robert Bosch Corp., 121 Corporate Blvd., South Plainfield, N.J. and Zanasi Ima Group, Bologna, Italy. As mentioned previously, a critical element in the process of the present invention is the proper water content of the hard gelatin capsule that is used to shrink about the caplet medicament. If the moisture content of the capsule is too low, or if the gelatin film dries out, the capsule will not sufficiently shrink about the caplet upon the application of heat to be useful. If the moisture content on the other hand is too high, excessive shrinking occurs and the short overlap defect becomes prevalent.

In order to overcome the moisture problem, the hard gelatin capsules can be heated in a sealed cavity or environmental chamber whose temperature and relative humidity are maintained at a constant. The climatic chamber allows the use of lower shrink temperatures than that of the sealed cavity and thereby generally gives better results. The relative humidity is kept sufficiently high, between approximately 50% and 90% and preferably 60% and 80% so as to prevent the capsules from drying out during shrinkage. Temperatures are best maintained from about 50° C. to about 100° C. with a preferred range of from about 65° C. to about 75° C. It was also found that the time in which the heat was applied played an important factor as short exposure times resulted in little or no shrinkage and bonding while too long an exposure resulted in excessive shrinkage and little to no overlap of the cap and body. Generally, the capsules can be heated from approximately 30 sec. to about 600 sec., with a preferred range of from about 90 sec. to 360 sec.

The following examples are provided to better describe and define the process and capsules of the present invention. They are for illustrative purposes only and it is realized that minor variations or modifications can be made thereto and therefore these examples should not be regarded as limiting the spirit and scope of the claims that follow.

EXAMPLE 1

The two halves of the gelatin capsules can be placed about the medicament caplet core either manually or mechanically by one of any number of commercially available encapsulation machines known in the art. Using a Blue M humidity chamber, five (5) samples of six (6) caplets each were bonded using different temperature and humidity parameters for different exposure times. The caplets used were placebos manufactured by either Perrigo, Inc. or Bristol Myers and they were placed within Supro C transparent hard gelatin capsules. Table II shows the percentage of tablets exhibiting defects for each of the parameters tested.

TABLE II

| T (°C.) | % RH | Exposure Time (sec.) | % Defects |
|---------|------|----------------------|-----------|
| 65 | 75 | 120 | 17 |
| 68 | 70 | 180 | 7 |
| 70 | 70 | 120 | 8 |
| 72 | 70 | 120 | 3 |

Clearly, these ranges produced results which can be applied to large scale commercial applications.

What I claim is:

1. A method for producing a simulated, tamper-resistant medicament capsule comprising the steps of:
   (a) inserting a generally ovoid and cylindrically shaped medicament into a first body portion of a two-part capsule, whose components have a moisture content of from about 11 to about 17% by weight;
   (b) joining a second cap portion thereof over the uncovered portion of the medicament to a point where both portions substantially overlap one another and;
   (c) applying energy in the form of heat in a humid atmosphere to shrink said capsule about said medicament for a sufficient time so that said capsule is fused about said medicament, wherein said heat is applied in the temperature range of approximately 50 C. to about 100 C., and said heat is applied in a chamber wherein the atmospheric relative humidity is from about 50% to about 90%.

2. The method of claim 1 wherein said capsule is comprised of a material selected from the group consisting of gelatin, starch, sugar gelatin, gelatin glycerin and mixtures thereof.

3. An encapsulated tamper-resistant medicament produced by the steps consisting of:
   (a) inserting a caplet comprised of said medicament into a first body portion of a two-part capsule, whose components have a moisture content of from about 11 to about 17% by weight;
   (b) joining a second cap portion of said capsule over the uncovered portion of the medicament to a point where both portions substantially overlap one another so as to completely encapsulate said caplet; and
   (c) applying energy in the form of heat in a humid atmosphere to shrink said capsule portions about said caplet for a sufficient time so that said capsule is fused about said capsule, wherein said heat is applied in a temperature range of from about 50 C. to about 100 C. and in an atmosphere with a relative humidity of from about 50% to about 90%.

4. The encapsulated medicament of claim 3 wherein said capsule is comprised of materials selected from the group consisting of gelatin, starch, sugar gelatin, gelatin-glycerin and mixtures thereof.

5. The encapsulated medicament of claim 4 wherein said gelatin capsule adheres to the surface of said caplet.

6. The method of claim 1 wherein said heat is applied to said capsuled medicament for a time period of about 60 to about 600 secs.

7. The method of claim 6 wherein said capsule, after the application of said heat, shrinks to substantially the same size as the volume defined by the perimeter of the surface area of said medicament.

8. The method of claim 7 wherein said overlapping portions of the gelatin capsule after the application of said heat become fused about a portion of the longitudinal axis of said medicament.

9. The encapsulated medicament of claim 3 wherein said heat is applied to said capsule for a time period of about 60 secs. to about 600 secs.

* * * * *